United States Patent [19]

Nihira et al.

[11] 4,339,721

[45] Jul. 13, 1982

[54] ELECTROSTATIC VOLTMETER

[75] Inventors: Yasuo Nihira; Takuya Hosoda, both of Tokyo, Japan

[73] Assignee: Ando Electric Co., Ltd., Tokyo, Japan

[21] Appl. No.: 153,234

[22] Filed: May 27, 1980

[30] Foreign Application Priority Data

Jun. 6, 1979 [JP] Japan .............................. 54-76766[U]
Jun. 19, 1979 [JP] Japan .............................. 54-83765[U]

[51] Int. Cl.³ ............................................ G01N 27/00
[52] U.S. Cl. ..................................... 324/457; 324/458
[58] Field of Search ......................... 324/72, 457, 458

[56] References Cited

U.S. PATENT DOCUMENTS 4,147,981 4/1979 Williams .............................. 324/458
4,205,267 5/1981 Williams .............................. 324/458

Primary Examiner—Michael J. Tokar
Attorney, Agent, or Firm—Blanchard, Flynn, Thiel, Boutell & Tanis

[57] ABSTRACT

An electrostatic voltmeter for measuring the surface potential of a charged body, includes a detecting electrode locatable adjacent to the charged body, and a vibrating element having a pair of parallel spaced legs between which the detecting electrode is disposed in spaced relation. The vibrating element is vibratable such that the legs move toward and away from the charged body. The vibrating element may extend transversely or parallel to a line connecting the charged body and the detecting electrode.

7 Claims, 7 Drawing Figures

ELECTROSTATIC VOLTMETER

BACKGROUND OF THE INVENTION

1. Field of the Invention

The present invention relates to an electrostatic voltmeter having a vibrating element adjacent to a detecting electrode for measuring the surface potential of a charged body disposed adjacent to the detecting electrode.

2. Prior Art

One known electrostatic voltmeter of the capacitive division type includes a detecting electrode which vibrates toward and away from a charged body to cause induced electric charge on the detecting electrode to be increased and reduced in synchronism with the vibration of the detecting electrode so as to produce an alternating signal. While such an electrostatic voltmeter is of high resolution, it is complicated in structure and costly to manufacture due to the vibrating electrode.

SUMMARY OF THE INVENTION

According to the present invention, an electrostatic voltmeter includes a fixed detecting electrode locatable in confronting relation to a charged body to be measured, and a vibrating element such as in the form of a tuning fork, having a pair of parallel vibrating legs between which the detecting electrode is disposed in spaced relation therewith. The vibrating element is vibrated such that the legs move toward and away from the charged body. As the vibrating element vibrates, the detecting electrode produces an alternating signal proportional to the surface potential of the charged body, the alternating signal being amplified by an amplifier before being read or measured. According to an embodiment of the present invention, the vibrating legs extend substantially at a right angle to a line connecting the charged body and the detecting electrode, and have a width greater than that of the detecting electrode. The detecting electrode is located away from the charged body within the width of the vibrating legs. A detecting element according to another embodiment is also in the form of a tuning fork having a pair of legs lying one on each side of the detecting electrode substantially parallel to a line connecting the charged body and the detecting element.

It is an object of the present invention to provide an electrostatic voltmeter which is relatively small in size, simple in structure, and inexpensive to manufacture.

Another object of the present invention is to provide an electrostatic voltmeter which is of high resolution with a minimized error in measurement.

The above and other objects, features and advantages of the present invention will become apparent from the following description when taken in conjunction with the accompanying drawings which illustrate preferred embodiments by way of example.

DETAILED DESCRIPTION

Figure 1:
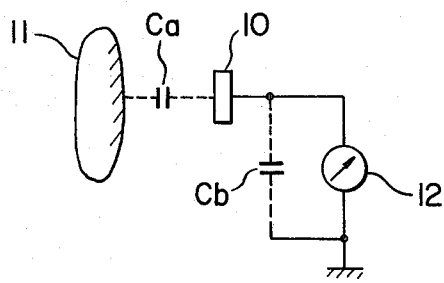
FIG. 1 is a diagrammatic view showing the general principle of an electrostatic voltmeter.

An electrostatic voltmeter includes a detecting electrode which is placed in confronting relation to a charged body to be measured for its surface potential. A potential is induced on the detecting electrode that is proportional to the electric field around the detecting electrode, which electrical field is in turn proportional to the surface potential of the charged body. FIG. 1 illustrates such principle of an electrostatic voltmeter. The electrostatic voltmeter shown in FIG. 1 includes a detecting electrode 10 to be placed in confronting relation to a charged body 11 to be measured for its surface potential, a potential display meter 12. Designated at Ca is an electrostatic capacity between the charged body 11 and the detecting electrode 10, and Cb an electrostatic capacity between the detecting electrode 10 and the ground. With such an arrangement, the following equation can be established;

$$Vd = \frac{Ca}{Ca + Cb} Vs \qquad (1)$$

where Vd represents the surface potential of the charged body 11 and Vs the potential of the detecting electrode 10. Thus, the surface potential Vd can be measured at the detecting electrode 10 through capacitive division.

Figure 2:
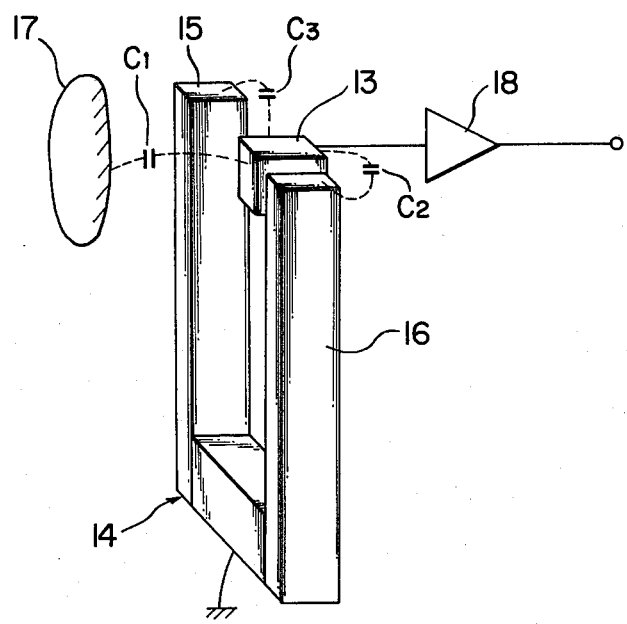
FIG. 2 is a schematic perspective view, partly shown in block diagram, of an electrostatic voltmeter according to a first embodiment of the present invention.
Figure 3:
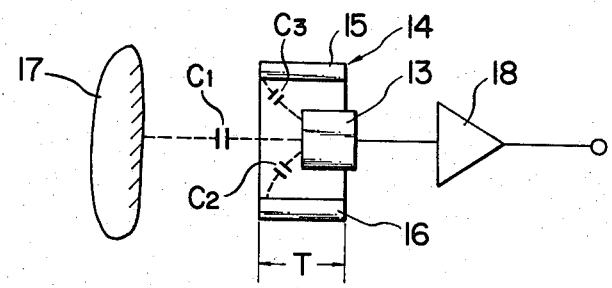
FIG. 3 is a plan view of the electrostatic voltmeter shown in FIG. 2.

According to a first embodiment of the present invention, an electrostatic voltmeter shown in FIGS. 2 and 3 comprises a fixed detecting electrode 13 and a vibrating element 14 such as in the form of a tuning fork including a pair of parallel spaced legs 15, 16 between which the detecting electrode 13 is disposed in spaced relation thereto. The vibrating element 14 is made of conductive material and grounded. The detecting electrode 13 is placed in confronting relation to a charged body 17 to be measured for its surface potential, and is electrically connected to an amplifier 18. The vibrating legs 15, 16 extend substantially at a right angle to a line connecting the charged body 17 and the detecting electrode 13.

As best shown in FIG. 3, the vibrating legs 15, 16 have a width T which is greater than that of the detecting electrode 13, which is located remotely from the charged body 17 substantially within the width T of the legs 15, 16. Thus, the legs 15, 16 have confronting surface portions with nothing whatsoever positioned in between. The detecting electrode 13 has a pair of opposite side surfaces facing the confronting surfaces, respectively, of the legs 15, 16, and a transverse surface facing the charged body 17 and lying substantially intermediate the width T of the legs 15, 16.

In operation, the vibrating element 14 is vibrated such that the legs 15, 16 move in the transverse direction thereof alternately toward and away from the charged body 17 while the detecting electrode 13 is being immovably held therebetween. The vibrating movement of the legs 15, 16 causes the electrostatic capacity $C_1$ between the charged body 17 and the detecting electrode 13 to alternately increase and decrease, and at the same time causes the electrostatic capacities $C_2$, $C_3$ between the detecting electrode 13 and the legs 15, 16, with the result that the detecting electrode 13 produces an alternating signal proportional to the surface potential Vs of the charged body 17.

The maximum value $C_1$ max of the capacity $C_1$ can be obtained when the legs 15, 16 are positioned farthest from the detecting electrode 13 because when the legs 15, 16 approach the grounded detecting electrode 13, electric lines of force from the charged body 17 reach the legs 15, 16 as well as the detecting electrode 13, with the electric lines of force that reach the detecting electrode 13 being reduced.

When the legs 15, 16 are the closest to the detecting electrode 13, we have the following equations:

$$C_2 = C_2 \text{ min} + \Delta C \qquad (2)$$

$$C_3 = C_3 \text{ min} + \Delta C \qquad (3)$$

where $C_2$ min, $C_3$ min represent capacities $C_2$, $C_3$, respectively, when the legs 15, 16 are positioned farthest from the detecting electrode 13, and $\Delta C$ represents a change in the capacities $C_2$, $C_3$ when the legs 15, 16 are positioned closest to the detecting electrode 13.

The following equation is also established:

$$C_1 = C_1 \text{ max} - \Delta C_1 \qquad (4)$$

where $C_1$ represents a change in the capacity $C_1$ when the legs 15, 16 are positioned closest to the detecting electrode 13.

Since the electrostatic voltmeter shown in FIGS. 2 and 3 are also of the capacitive division type, $$Vd = \frac{C_1}{C_1 + C_2 + C_3} Vs = \frac{C_1}{C_1 + 2\Delta C + C_2 \text{ min} + C_3 \text{ min}} Vs.$$

When $\Delta C >> C_2$ min $+ C_3$ min, that is, the capacity change $\Delta C$ experienced when the legs 15, 16 are positioned closest to the detecting electrode 13 is sufficiently larger than the capacities $C_2$ min, $C_3$ min with the legs 15, 16 positioned farthest from the detecting electrode 13, then we have the equation:

$$Vd = \frac{C_1}{C_1 + 2\Delta C} Vs \qquad (5)$$

The equation (5) is concerned with a relation between the potential Vd induced on the detecting electrode 13 by the vibration of the legs 15, 16 and the surface potential Vs of the charged body 17. A periodical potential change $\Delta Vd$ due to the vibration of the legs 15, 16 can be expressed as follows:

$$\Delta Vd = Vs - \frac{C_1}{C_1 + 2\Delta C} Vs = \frac{2\Delta C}{C_1 + 2\Delta C} Vs \qquad (6)$$

The potential change $\Delta Vd$ constitutes an alternating signal proportional to the surface potential Vs of the charged body 17, and accordingly can be amplified by the amplifier 18 for high-resolution measurement of the surface potential.

The substitution of the equation (4) in the electrostatic capacity $C_1$ of the equation (6) gives $$\Delta Vd = \frac{2\Delta C}{C_1 \text{ max} - \Delta C_1 + 2\Delta C} Vs \qquad (7)$$

from which it is understood that the change $\Delta C_1$ in the capacity $C_1$ serves to increase the potential change $\Delta Vd$. By inserting the detecting electrode 13 partly between the legs 15, 16, the capacity change $\Delta C_1$ can be increased so that the potential change $\Delta Vd$ is the more increased.

Figure 4:
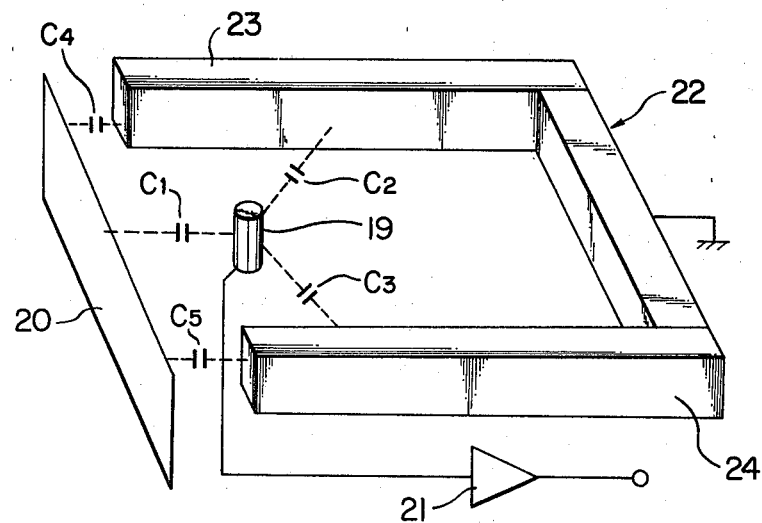
FIG. 4 is a schematic perspective view partly shown in block diagram, of an electrostatic voltmeter according to a second embodiment.
Figure 5:
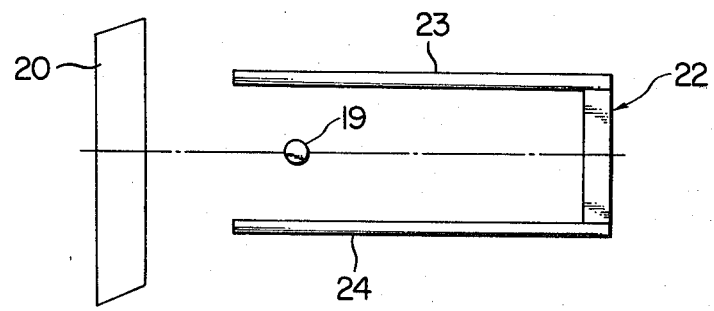
FIG. 5 is a plan view of the electrostatic voltmeter shown in FIG. 4.

FIGS. 4 and 5 show a second embodiment, in which a electrostatic voltmeter comprises a fixed detecting electrode 19 confronting a charged body 20 to be measured for its surface potential, an amplifier 21 electrically connected to the detecting electrode 19, and a vibrating element 22 in the form of a tune fork of conductive material. The vibrating element 22 is grounded and comprises a pair of parallel spaced legs 23, 24 disposed one on each side of the detecting electrode 19 in spaced relation. The vibrating element 22 lies substantially parallel to a line connecting the detecting electrode 19 and the charged body 20.

In operation, the vibrating element 22 is vibrated such that the legs 23, 24 move in the longitudinal direction thereof alternatively toward and away from the charged body 17 with the detecting electrode 19 being held immovably. While the vibrating element 22 is thus vibrated, the electrostatic capacity $C_1$ between the charged body 20 and the electrode 19, and the electrostatic capacities $C_2$, $C_3$ between the electrode 19 and the legs 23, 24 are caused to increase and decrease alternately, thereby enabling the detecting electrode 19 to produce an alternate signal proportional to the surface potential Vs of the charged body.

The minimum valve $C_1$ min of the capacity $C_1$ can be obtained when the legs 23, 24 are positioned closest to the detecting electrode 19 because electric lines of force from the charged body 20 that reach the detecting electrode 19 are reduced due to the shielding of the grounded legs 23, 24.

When the legs 23, 24 are the farthest from the detecting electrode 19, we have the following equations:

$$C_2 = C_2 \text{ max} - \Delta C \qquad (8)$$

$$C_3 = C_3 \text{ max} - \Delta C \qquad (9)$$

where $C_2$max, $C_3$ max represent capacities $C_2$, $C_3$, respectively, when the legs 23, 24 are positioned closest to the detecting electrode 19, and $\Delta C$ represents a change from the capacities $C_2$ max, $C_3$ max.

The following equation is also established:

$$C_1 = C_1 \text{ min} + \Delta C_1 \qquad (10)$$

where $\Delta C_1$ represents a change in the capacity when the legs 23, 24 move away from the detecting electrode 19.

Since the electrostatic voltmeter shown in FIGS. 4 and 5 are also of the capacitive division type, $$Vd = \frac{C_1}{C_1 + C_2 + C_3} Vs \qquad (11)$$

Because $C_2 \approx C_3$ and the capacity $C_1$ is extremely small as compared with the capacities $C_2$, $C_3$, $$Vd = \frac{C_1}{C_2 + C_3} Vs \qquad (12)$$

$$= \frac{C_1 \min + \Delta C_1}{C_2 + C_3} Vs$$

When the legs 23, 24 are positioned closest to the detecting electrode 19, the capacity $C_1$ min is sufficiently smaller than the capacity change $\Delta C_1$. Therefore, we have $$Vd = \frac{\Delta C_1}{C_2 + C_3} Vs \qquad (13)$$

From the equation (13), a periodical potential change $\Delta Vd$ due to the vibration of the legs 23, 24 can be expressed as follows:

$$\Delta Vd = \frac{\Delta C_1}{C_2 \max + C_3 \max - 2\Delta C} Vs \qquad (14)$$

The potential change $\Delta Vd$ constitutes an alternating signal proportional to the surface potential Vs of the charged body 20, and accordingly can be amplified by the amplifier 21 for high-resolution measurement of the surface potential.

As shown in FIG. 4, when the legs 23, 24 of the vibrating element 22 are disposed close to the charged body, there are produced electrostatic capacities $C_4$, $C_5$ between the charged body 20 and the legs 23, 24, with the result that the measured surface potential Vs of the charged body 20 becomes lower than the real value. The arrangement of FIG. 4 allows such unwanted additional capacities to be held at a minimum.

Figure 6:
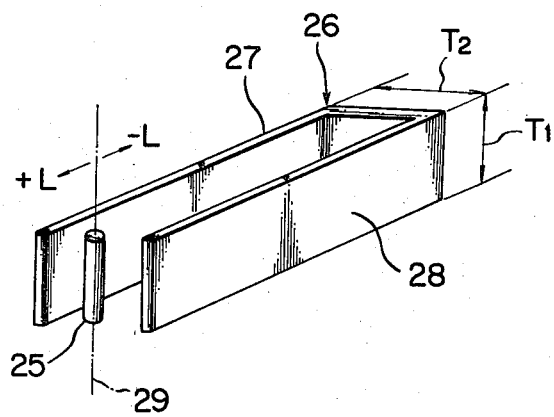
FIG. 6 is a perspective view of a detecting electrode and a vibrating element arranged for measurement of detection sensitivity.

FIG. 6 illustrates an example of the second embodiment of FIGS. 4 and 5. A detecting electrode 25 is of a cylindrical shape having a diameter of 0.5 mm, and a vibrating element 26 has a pair of parallel legs 27, 28 having a width $T_1$ of 3 mm, the distance $T_2$ between the legs 27, 28 being 2 mm. The distal ends of the vibrating legs 27, 28 are spaced apart from a charged body (not shown) by a distance of 5 mm. Indicated at +L is a distance the electrode 25 is moved from a reference position line 29, which is the one connecting the distal ends of the vibrating legs 27, 28, toward the charged body, and at −L is a distance the electrode 25 is moved from the reference position line 29 away from the charged body.

Figure 7:
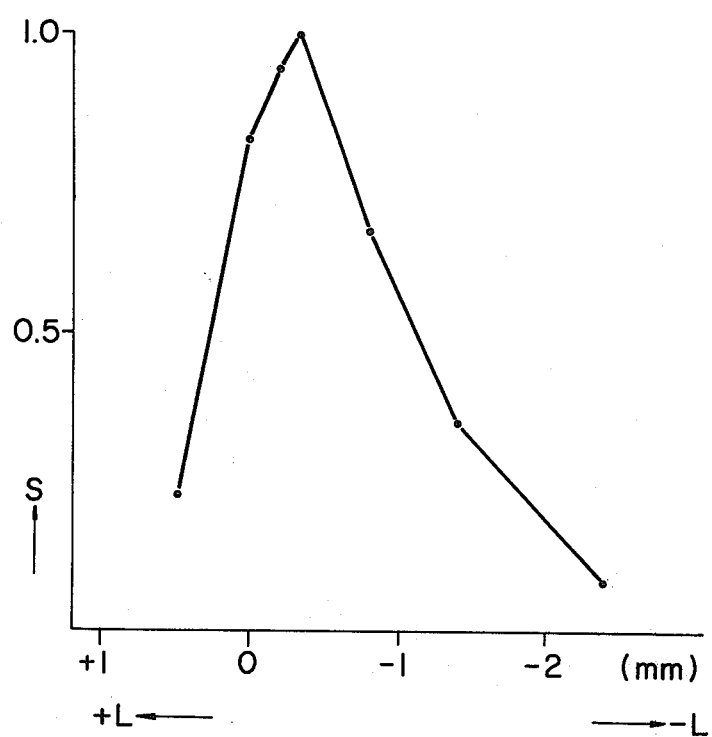
FIG. 7 is a graph showing a relation between positions of the detecting electrode and changes in the detection sensitivity the components shown in FIG. 6.

As illustrated in FIG. 7, detection sensitivity S becomes maximum when the detecting electrode 19 is located slightly off the reference position line 29 away from the charged body, that is, the electrode 19 is disposed about −0.5 mm from the reference position line 29 between the legs 23, 24. With the electrode 19 thus positioned, the surface potential of the charged body can most effectively be converted into a detectable alternating signal which is picked up from the detecting electrode 19.

Although certain preferred embodiments have been shown and described in detail, it should be understood that many changes and modifications may be made therein without departing from the scope of the appended claims.

What is claimed is:

1. An electrostatic voltmeter for measuring the surface potential of a charged body through capacitive division, comprising a detecting electrode locatable in confronting relation to the charged body, and a vibrating element including a pair of parallel spaced legs between which said detecting electrode is disposed in spaced relation, said vibrating element being vibratable to enable said legs to move toward and away from the charged body.

2. An electrostatic voltmeter according to claim 1, said vibrating element being locatable so as to extend transversly to a line connecting the charged body and said detecting electrode, whereby said legs are movable in the transverse direction thereof, said detecting electrode having a width smaller than that of said legs and being locatable remotely from the charged body substantially within the width of said legs, and said legs having surface portions confronting directly each other at a position closer to the charged body.

3. An electrostatic voltmeter according to claim 1, said vibrating element being locatable so as to lie substantially parallel to a line connecting the charged body and said detecting electrode, whereby said legs are movable in the longitudinal direction thereof.

4. In an electrostatic voltmeter for measuring, through capacitive division, the surface potential of a charged body at a charged body location at the front of said voltmeter comprising a vibrating element having a pair of parallel spaced legs vibratable with respect to said charged body location in spaced opposed relation thereto, the improvement comprised by:
said vibrating element having said legs arranged to vibrate toward and away from the charged body; and
a nonvibrating detecting electrode fixed with respect to said charged body location in spaced opposed relation thereto, said detecting electrode being spaced between said legs, which legs are vibratable with respect to said detecting electrode.

5. An electrostatic voltmeter according to claim 4 including an amplifier electrically driven by said fixed detecting electrode and in which the vibrating element is of conductive material and is grounded.

6. An electrostatic voltmeter according to claim 4 in which the extent of said vibrating legs, in a direction toward and away from charged body location, exceeds the width of said fixed detecting electrode and said detecting electrode has a surface facing toward said charged body location offset from said charged body location within said extent of said vibrating legs, such that said vibrating legs have surfaces closer to said charged body location than does said detecting electrode spaced therebetween.

7. An electrostatic voltmeter according to claim 4 including first and second and third electrostatic capacities between said fixed detecting electrode and, respectively, said charged body and one said leg and the other said leg, said first and second and third electrostatic capacities all being changeable in response to said vibration of said legs toward and away from said charged body position.

* * * * *